Figure 1:
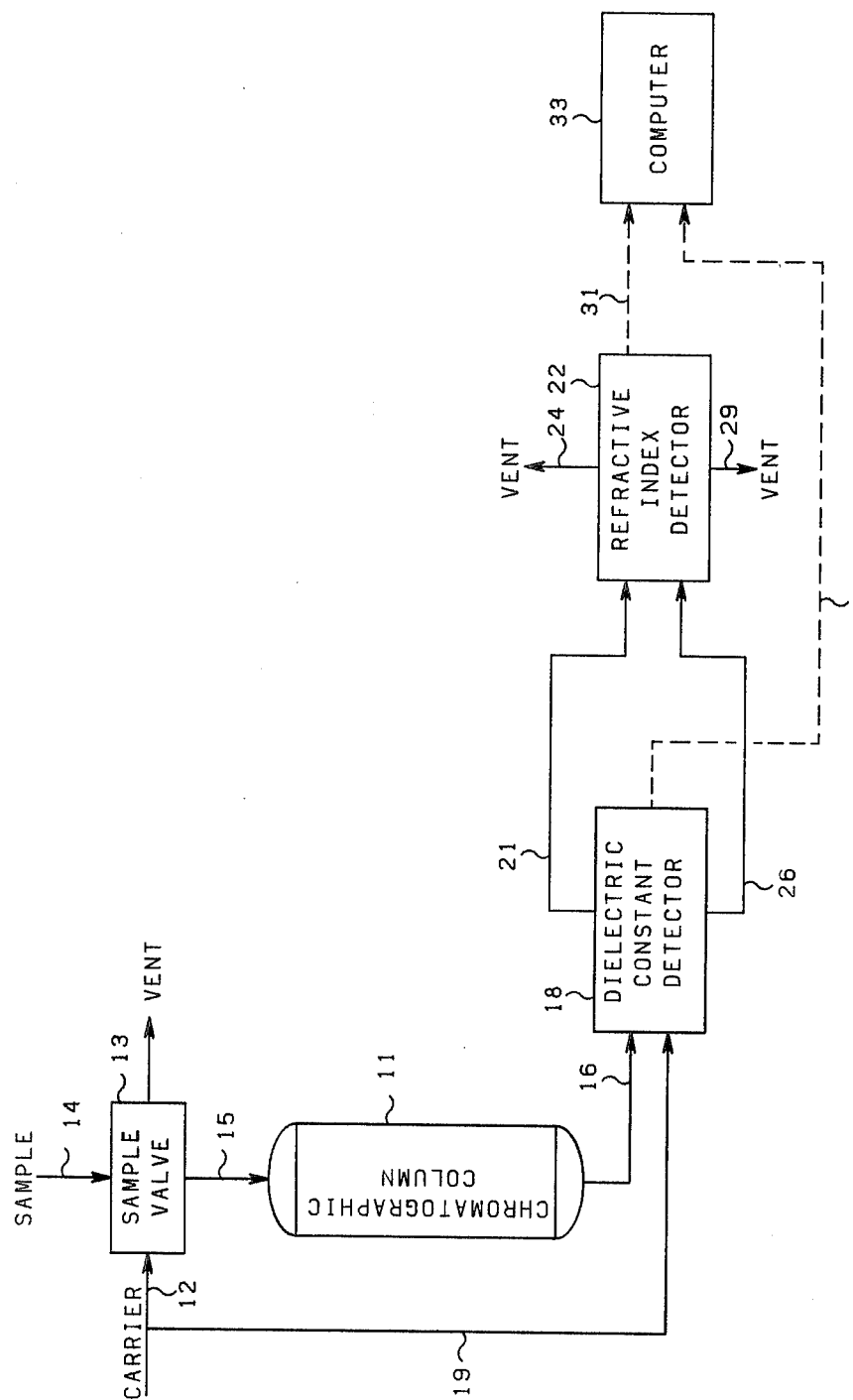

United States Patent [19]

Sanford et al.

[11] 4,254,656
[45] Mar. 10, 1981

[54] CHROMATOGRAPHIC ANALYSIS WITHOUT CALIBRATION USING DUAL DETECTORS

[75] Inventors: Richard A. Sanford; William H. Dennis, both of Bartlesville, Okla.

[73] Assignee: Philips Petroleum Company, Bartlesville, Okla.

[21] Appl. No.: 74,709

[22] Filed: Sep. 12, 1979

[51] Int. Cl.³ .......................................... G01N 31/08
[52] U.S. Cl. .............................. 73/61.1 C; 210/198.2; 422/70
[58] Field of Search .................. 73/61.1 C; 210/31 C, 210/198 C; 422/70

[56] References Cited

U.S. PATENT DOCUMENTS

| | | | |
|---|---|---|---|
| 3,759,816 | 9/1973 | Pretorius et al. | 204/299 |
| 3,997,298 | 12/1976 | McLafferty et al. | 73/61.1 C X |
| 4,066,405 | 1/1978 | Henkin | 23/230 B |

*Primary Examiner*—John Petrakes
*Assistant Examiner*—Joseph W. Roskos

[57] ABSTRACT

A quantitative analysis of the concentration of an eluted component, the dielectric constant of an eluted component and/or the refractive index of the eluted component is obtained using a chromatographic analyzer in combination with both a refractive index detector and a dielectric constant detector without the need to calibrate either the refractive index detector or the dielectric constant detector for each component in a sample. The dielectric constant detector and the refractive index detector are utilized to analyze a sample provided from a chromatographic analyzer. The concentration of the eluted component is a function of the magnitude of the output from each of the detectors. In like manner, the dielectric constant of the eluted component and the refractive index of the eluted component is a function of the output from the two detectors. The magnitude of the output from the two detectors is combined to give the concentration of an eluted component, the dielectric constant of the eluted component and the refractive index of the eluted component without the necessity of calibrating the detectors for each component in a sample.

8 Claims, 3 Drawing Figures

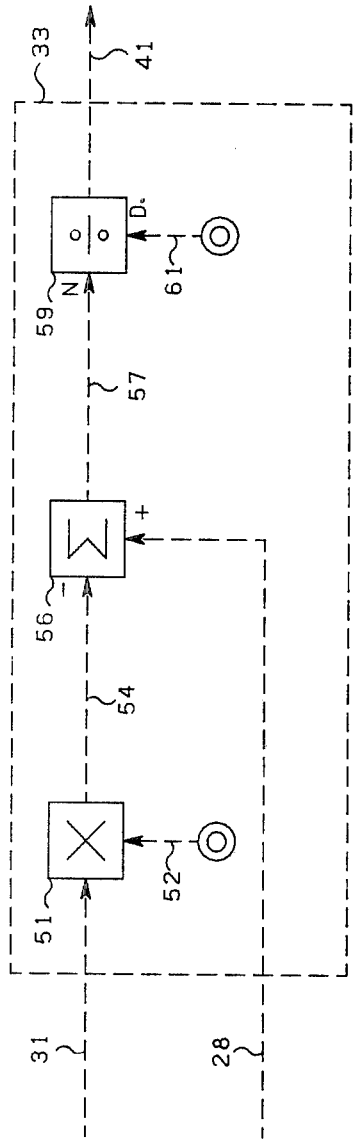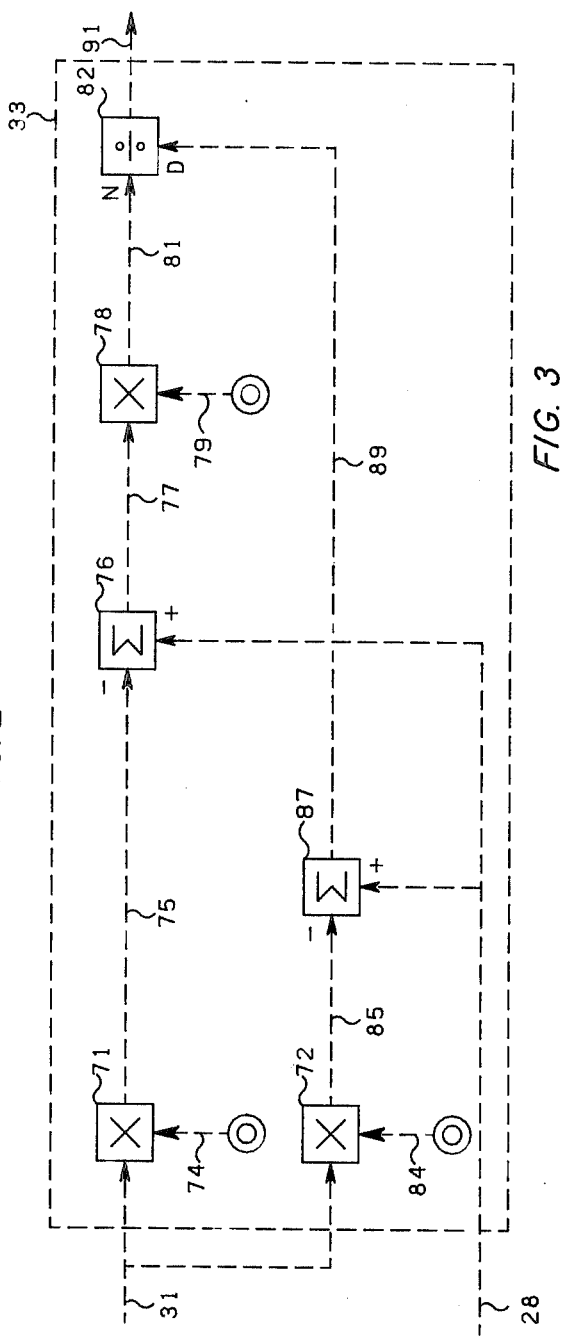
FIG. 2
FIG. 3

CHROMATOGRAPHIC ANALYSIS WITHOUT CALIBRATION USING DUAL DETECTORS

This invention relates to chromatography. In a specific aspect this invention relates to method and apparatus for obtaining a quantitative analysis of the concentration of an eluted component, the dielectric constant of an eluted component and/or the refractive index of the eluted component without the necessity of calibrating a chromatographic analyzer detector for each component in a sample.

A chromatographic analyzer is an analytical instrument that is used to separate in time and individually detect the constituents of a sample to be analyzed. The chromatographic analyzer typically includes an analytical column through which a carrier fluid (other terms such as solvent or eluent are commonly utilized) is passed continuously. The sample (often referred to as solute) to be analyzed is injected into the carrier stream and is thus carried through the analytical column. The sample constituents are carried through the analytical column at different velocities and in this manner the sample constituents are separated in time.

A detector is employed to detect the separate constituents and the detector output signal typically is plotted as a function of time to produce what is termed a chromatogram. As each sample component is eluted from the column, the component produces a sharp increase in the detector output signal amplitude, which increase appears as a peak or spike in the chromatogram.

The response of a dielectric constant detector is given by the equation $$E_{DC} = K_{DC}[(P_S/V_S)/(P_E/V_E) - 1]C_S \quad (I)$$

where $E_{DC}$ = output of a dielectric constant detector,
$K_{DC}$ = dielectric detector constant,
$P_S$ = molar polarization of the solute,
$V_S$ = molar volume of the solute,
$P_E$ = molar polarization of the eluent,
$V_E$ = molar volume of the eluent, and
$C_S$ = concentration of the solute.

The response of a refractive index detector is given by $$E_{RI} = K_{RI}[(R_S/V_S)/(R_E/V_E) - 1]C_S \quad (II)$$

where $E_{RI}$ = output of a refractive index detector,
$K_{RI}$ = refractive index detector constant,
$R_S$ = molar refraction of the solute,
$V_S$ = molar volume of the solute,
$R_E$ = molar refraction of the eluent,
$V_E$ = molar volume of the eluent, and
$C_S$ = concentration of the solute.

It is apparent from equations (I) and (II) that the output from the dielectric constant detector is a function of both the concentration of the solute and the molar polarization of the solute which is related to the dielectric constant of the solute. In like manner, the output of the refractive index detector is related to both the concentration of the solute and the molar refraction of the solute which is a function of the refractive index of the solute. It can thus be seen that the molar polarization of a solute must be known before a dielectric constant detector can be utilized to quantitatively determine the concentration of the solute. In like manner, the molar refraction of a solute must be known before a refractive index detector can be utilized to determine the concentration of a solute. Generally, this is accomplished by what is known as calibration. A solute having a known concentration of a particular component is run through either a dielectric constant detector or a refractive index detector and the output of the detectors for a known concentration of a particular component is noted. This output can then be related directly to either the molar polarization or the molar refraction because the concentration of the component is known. Once the molar polarization or the molar refraction is known, a sample having an unknown concentration of the component can be analyzed and a quantitative analysis of the concentration of the solute made. In like manner, a detector may be calibrated by using components having a known molar polarization or a known molar refraction. The calibration of the detectors must be repeated for each component in the solute which is to be analyzed.

Calibration generally requires samples having known properties. Great care is required to obtain these samples and the standard is rarely absolute. Obviously the accuracy of the chromatographic analysis is dependent upon the calibration and is thus dependent upon the accuracy with which the characteristics of the samples are known. It is thus extremely desirable to provide a method for performing a chromatographic analysis without the need to continuously calibrate detectors. It is thus an object of this invention to provide method and apparatus for obtaining a quantitative analysis of the concentration of an eluted component, the dielectric constant of an eluted component and/or the refractive index of the eluted component without the necessity of calibrating a chromatographic analyzer detector for each component in a sample.

In accordance with the present invention, method and apparatus is provided whereby a dielectric constant detector and a refractive index detector is utilized in combination with a chromatographic column to obtain a quantitative analysis of the concentration of the individual components in a sample without the necessity of calibrating either the dielectric constant detector or the refractive index detector for each component in the sample. The dielectric constants of the individual components in the sample and the refractive index of the individual components in the sample may also be obtained without the need for calibrating either the refractive index detector or the dielectric constant detector for each component in the sample.

The solute which is to be analyzed must be substantially non-polar while the carrier fluid or eluent must be substantially polar. The accuracy of the analysis of the present invention is a function of the non-polarity of the solute. The greater the non-polarity of the solute, the greater the accuracy of the analysis of the present invention.

As has been previously stated, Equation (I) gives the response of a dielectric constant detector while Equation (II) gives the response of a refractive index detector. Also as has been previously stated, the molar polarization P is a function of the dielectric constant. This relationship is given approximately by the equation $$\frac{P}{V} = \frac{DC - 1}{DC + 2} \quad \text{(III)}$$

where
DC = dielectric constant.
In like manner, the molar refraction is approximately related to the refractive index by the equation $$\frac{R}{V} = \frac{RI^2 - 1}{RI^2 + 2} \quad \text{(IV)}$$

where
RI = refractive index.
For solutes which are substantially non-polar, $P_S/V_S$ is substantially equal to $R_S/V_S$. Also, for eluents which are polar, $P_E/V_E$ does not equal $R_E/V_E$. Solving Equation (I) for $P_S/V_S$ gives $$P_S/V_S = \frac{(E_{DC} + K_{DC}C_S)(P_E/V_E)}{K_{DC}C_S} \quad \text{(V)}$$

Solving Equation (II) for $R_S/V_S$ gives $$R_S/V_S = \frac{(E_{RI} + K_{RI}C_S)(R_E/V_E)}{K_{RI}C_S} \quad \text{(VI)}$$

As has been previously stated, $P_S/V_S$ is substantially equal to $R_S/V_S$ if the solute is substantially non-polar. Thus Equations (V) and (VI) can be combined to give $$\frac{(E_{DC} + K_{DC}C_S)(P_E/V_E)}{K_{DC}C_S} = \frac{(E_{RI} + K_{RI}C_S)(R_E/V_E)}{K_{RI}C_S} \quad \text{(VII)}$$

Rearranging Equation (VII) and cancelling like terms gives $$E_{DC} - \frac{R_E K_{DC}}{P_E K_{RI}} E_{RI} = \frac{K_{DC}(R_E - P_E)}{P_E} C_S \quad \text{(VIII)}$$

Setting
$$K_1 = \frac{R_E K_{DC}}{P_E K_{RI}}$$

and
$$K_2 = \frac{K_{DC}(R_E - P_E)}{P_E}.$$

gives
$$E_{DC} - K_1 E_{RI} = K_2 C_S \quad \text{(IX)}$$

The constants $K_1$ and $K_2$ may be determined by analyzing two components in a sample, where the concentration of each component is known. Since $E_{DC}$ and $E_{RI}$ would be known and the concentration is known, there are two equations with two unknowns and $K_1$ and $K_2$ can be easily solved for. Once $K_1$ and $K_2$ have been determined, these constants do not change for other components in a sample. Thus, the remaining components in a sample or a totally new sample can be analyzed without the need to calibrate the dielectric constant detector or the refractive index detector for each component in the sample. As is shown in Equation (IX), the concentration of each component in the sample will be a function of the magnitude of the output of the dielectric constant detector and the magnitude of the output from the refractive index detector. Once the constants $K_1$ and $K_2$ have been determined, the concentration of any component in a sample may be determined simply by noting the output from the dielectric constant detector and refractive index detector so long as the carrier fluid remains unchanged, the component is substantially non-polar, and the carrier fluid is substantially polar.

It should be noted that Equation (IX) does not involve the molar refraction, molar polarization or the molar volume of the component in the sample which is being eluted. It is this factor which enables the outputs from the detectors to be utilized directly to derive the concentration of the component without the need to calibrate the detectors for each component in the sample.

As has been previously noted, for a substantially non-polar component in a sample, $P_S/V_S$ is substantially equal to $R_S/V_S$. Thus, the output from the dielectric constant detector and the refractive index detector may be utilized to derive the molar polarization of the component in the sample which will be equal to the molar refraction of the component in the sample which is being eluted. Equations (III) and (IV) can then be utilized to derive either the dielectric constant for the component in the sample or the refractive index for the component in the sample. Again, no calibration is required for each component in the sample. Solving Equation (I) for $C_S$ gives $$C_S = \frac{E_{DC}/K_{DC}}{(P_S/V_S)/(P_E/V_E) - 1} \quad \text{(X)}$$

Solving Equation (II) for $C_S$ gives $$C_S = \frac{E_{RI}/K_{RI}}{(R_S/V_S)/(R_E/V_E) - 1} \quad \text{(XI)}$$

Substituting Equation (XI) into Equation (X) and recognizing that $P_S/V_S$ is substantially equal to $R_S/V_S$ gives $$\frac{R_S}{V_S}\left(\frac{E_{DC}K_{RI}}{R_E/V_E} - \frac{E_{RI}K_{DC}}{P_E/V_E}\right) = E_{DC}K_{RI} - E_{RI}K_{DC} \quad \text{(XII)}$$

Multiplying through by $\frac{R_E/V_E}{K_{RI}}$ gives $$\frac{R_S}{V_S}\left[E_{DC} - E_{RI}\left(\frac{K_{DC}}{K_{RI}}\right)\left(\frac{R_E/V_E}{P_E/V_E}\right)\right] = \frac{R_E}{V_E}\left[E_{DC} - E_{RI}\left(\frac{K_{DC}}{K_{RI}}\right)\right] \quad \text{(XIII)}$$

Solving for $R_S/V_S$ gives $$\frac{R_S}{V_S} = \frac{\frac{R_E}{V_E}\left[E_{DC} - E_{RI}\left(\frac{K_{DC}}{K_{RI}}\right)\right]}{\left[E_{DC} - E_{RI}\left(\frac{K_{DC}}{K_{RI}}\right)\left(\frac{R_E/V_E}{P_E/V_E}\right)\right]} \quad \text{(XIV)}$$

Setting
$$K_3 = \frac{K_{DC}}{K_{RI}}$$

and
$$K_4 = \left(\frac{K_{DC}}{K_{RI}}\right)\left(\frac{R_E/V_E}{P_E/V_E}\right)$$

gives
$$\frac{R_S}{V_S} = \frac{\frac{R_E}{V_E}[E_{DC} - K_3 E_{RI}]}{[E_{DC} - K_4 E_{RI}]} \quad \text{(XV)}$$

Equation (XV) illustrates the relationship between the outputs of the dielectric constant detector and the refractive index detector and the ratio of the molar polarization to the molar volume. The constants $K_3$ and $K_4$ can be determined in the manner previously described for the constants $K_1$ and $K_2$. It is noted that Equation (XV) does not contain the concentration of the component and again the ratio of the molar polarization to the molar volume can be determined without calibrating the dielectric constant detector or the refractive index detector for each component in the sample. Either the dielectric constant of the component or the refractive index of the component may be determined from the ratio of the molar polarization to the molar volume utilizing either Equation III or Equation IV.

Other objects and advantages of the invention will be apparent from the brief description of the invention and the appended claims as well as from the detailed description of the drawing in which:

FIG. 1 is a representation of a chromatographic analyzer system employing both a dielectric constant detector and a refractive index detector.

The invention is described in terms of a specific chromatographic analyzer system. The invention is, however, applicable to other chromatographic analyzer systems and configurations.

Referring now to FIG. 1, here is shown a chromatographic column 11. A sample of a fluid to be analyzed is delivered to the sample valve 13 through conduit means 14. A conduit means 15 extends between the sample valve 13 and the inlet to the chromatographic column 11. A conduit means 16 extends between the outlet of the chromatographic column 11 and the sample inlet of the dielectric constant detector 18. Carrier fluid is passed to the reference portion of the dielectric constant detector 18 through conduit means 19 which is in fluid communication with conduit means 12. The carrier fluid is also provided through conduit means 12 to the sample valve 13. Carrier fluid may thus be provided through the sample valve 13 and the chromatographic column 11 to the sample input of the dielectric constant detector 18.

The effluent flowing through conduit means 16 flows through the sample portion of the dielectric constant detector 18 and then is provided through conduit means 21 to the sample inlet of the refractive index detector 22. The effluent flowing through conduit means 21 is vented from the sample side of the refractive index detector 22 through conduit means 24. The carrier fluid flowing through conduit means 19 flows out of the reference side of the dielectric detector 18 through conduit means 26 and is provided to the reference input of the refractive index detector 22. Carrier fluid is vented from the refractive index detector 22 through conduit means 29.

At the beginning of an analysis period, sample valve 13 is actuated to introduce a predetermined volume of sample into the carrier fluid flowing through the chromatographic column 11. The constituents of the sample are eluted in sequence and flow from the chromatographic column 11 through conduit means 16 to the sample side of the dielectric constant detector 18. From the dielectric constant detector 18, the constituents of the sample flow to the sample side of the refractive index detector 22. The dielectric constant detector 18 establishes an output signal 28 ($E_{DC}$) in response to a constituent in the sample. In like manner, the refractive index detector 22 establishes an output signal 31 ($E_{RI}$) in response to a constituent in the sample. Both signals 28 and 31 are supplied to computer means 33 which makes the calculations set forth in Equations (IX) and (XV). These calculations could be made by hand or by other computing means if desired.

The constants $K_1$ and $K_2$ of Equation IX may be established by using a solution which has a known concentration of two components. A sample of this solution is introduced through sample valve 13 to the chromatographic column 11 and the response of both the dielectric constant detector and the refractive index detector to a first component is noted. The response to the dielectric constant detector 18 and the refractive index detector 22 to a second component is also noted.

The concentration of the first component is given by Equation (IX) as $$C_1 = \frac{E_{DC} - K_1 E_{RI}}{K_2} \quad \text{(XVI)}$$

where $C_1$ is the concentration of the first component. The concentration of the second component is given by Equation (IX) as $$C_2 = \frac{E_{DC} - K_1 E_{RI}}{K_2} \quad \text{(XVII)}$$

where $C_2$ is the concentration of the second component. $C_1$ and $C_2$ are known and the response of the dielectric constant detector 18 and the refractive index detector 22 to each component will also be known. Thus, there are two equations with two unknowns. $K_1$ and $K_2$ can be easily solved for and these constants will not change as long as the carrier fluid does not change.

The constants $K_3$ and $K_4$ of Equation (XV) can be determined in the manner described for the constants $K_1$ and $K_2$. Instead of using a solution which has a known concentration of two components, a solution which has two components having a known ratio of molar polarization to molar volume is utilized.

After the constants $K_1$, $K_2$, $K_3$ and $K_4$ have been calculated, a sample may be introduced through the sample valve 13 into the chromatographic column 11. The response of the dielectric constant detector 18 and the refractive index detector 22 is noted for each component in the sample and Equation (IX) is utilized to calculate the concentration of each component in the sample. Equation (XV) is utilized to calculate the ratio of the molar polarization to the molar volume of each component in the sample. The refractive index of each component in the sample or the dielectric constant of each component in the sample can then be determined utilizing either Equation (III) or Equation (IV).

Any suitable, substantially non-polar solute may be analyzed in accordance with the present invention. The best analysis results have been obtained for normal alkanes such as pentane, hexane and the like and isoalkanes such as isopentane, isohexane and the like. Other suitable solutes are cycloalkanes such as cyclopentane, cyclohexane and the like; monoolefins such as pentene, hexene and the like; diolefins such as 1,4-pentadiene, 1,3-pentadiene and the like; and aromatics such as benzene, o-xylene, m-xylene and the like.

Any suitable, substantially polar eluent may be utilized. In general, eluents will have a low viscosity and must be a solvent for the particular solute being analyzed. Eluents such as tetrahydrofuran, ortho-dichlorobenzene, and the like are particularly suitable. Toluene is particularly suitable if the solute has a very low polarity or is completely non-polar.

The processing of the output signal 28 from the dielectric constant detector 18 and the output signal 31 from the refractive index detector 22 to determine the concentration of a specific component in a sample is illustrated in FIG. 2. As has been previously stated, this can be accomplished in a plurality of ways but is preferably accomplished using a digital computer. The output 41 from the computer 33 will typically be a printout. Signal 31 ($E_{RI}$) is provided as an input to the multiplying block 51. A signal 52, which is representative of the constant $K_1$, is supplied as a second input to the multiplying block 51. The output signal 54 from the multiplying block 51 will thus be representative of $K_1E_{RI}$. Signal 54 is supplied from the multiplying block 51 to the subtrahend input of the summation block 56. Signal 28 ($E_{DC}$) is supplied to the minuend input of the summation block 56. The output signal 57 from the summation block 56 will be representative of $E_{DC}-K_1E_{RI}$. Signal 57 is supplied as an input to the dividing block 59. The dividing block 59 is also provided with signal 61 which is representative of the constant $K_2$. Signal 57 is divided by signal 61 to provide the concentration of the particular component in the sample. As has been previously stated, this concentration will generally be provided as a computer printout which is represented by signal 41.

The processing of signal 28 from the dielectric constants detector 18 and signal 31 from the refractive index detector 22 to obtain the ratio of the molar polarization to the molar volume of a particular component in the sample is illustrated in FIG. 3. Again, this calculation could be accomplished in a number of ways. Referring now to FIG. 3, signal 31 ($E_{RF}$) is provided as an input to the multiplying block 71 and is also provided as an input to the multiplying block 72. The multiplying block 72 is also provided with signal 74 which is representative of the constant $K_3$. Signal 31 is multiplied by signal 74 to provide signal 75 which is representative of $E_{RI}K_3$. Signal 75 is provided to the subtrahend input of the summing block 76. Signal 28 ($E_{DC}$) is provided to the minuend input of the summing block 76. Signal 75 is subtracted from signal 28 to provide signal 77 which is representative of $E_{DC}-K_3E_{RI}$. Signal 77 is provided as an input to the multiplying block 78. The multiplying block 78 is also provided with signal 79 which is representative of $R_E/V_E$. Signal 77 is multiplied by signal 79 to provide signal 81 which is representative of $(R_E/V_e)(E_{DC}-K_3E_{RI})$. Signal 81 is provided to the numerator input of the dividing block 82.

Signal 84 which is representative of the constant $K_4$ is also supplied to the multiplying block 72. Signal 31 is multiplied by signal 84 to provide signal 85 which is representative of $K_4E_{RI}$. Signal 85 is provided to the subtrahend input of the summing block 87. Signal 28 is provided to the minuend input of the summing block 87. Signal 85 is subtracted from signal 28 to provide signal 89 which is representative of $E_{DC}-K_4E_{RI}$. Signal 89 is provided to the denominator input of the dividing block 82. Signal 81 is divided by signal 89 to provide an output which is representative of the molar refraction of a component in a sample divided by the molar volume of a component in a sample. This output, which is commonly in the form of a computer printout, is represented as signal 91.

The invention has been described in terms of a preferred embodiment as illustrated in FIGS. 1–3. As has been previously stated, many different chromatographic analyzer configurations could be utilized. The calculations could be performed by hand but preferably a digital computer is programmed to perform the required calculations. Also, a simple analog configuration could be utilized to perform the required calculations. A commercially available refractive index detector which can be utilized in the present invention is the Model 401, manufactured by Waters Associates, Inc., Framingham, Mass. A commercially available dielectric constant detector is the Model 410, manufactured by Applied Automation, Inc., Bartlesville, Oklahoma. A commercially available digital computer which could be utilized is the Optichrom 2100 manufactured by Applied Automation, Inc.

While the invention has been described in terms of the presently preferred embodiments, reasonable variations and modifications are possible by those skilled in the art, within the scope of the described invention and the appended claims. In particular, the dielectric constant detector and the refractive index detector may be configured in parallel rather than in series as is illustrated in FIG. 1.

That which is claimed is:

1. Apparatus for obtaining an analysis of the concentration of a substantially non-polar component of a material comprising:
   a chromatographic separation column means;
   means for passing a stream of a carrier fluid, which is substantially polar, to said chromatographic separation column means;
   means for injecting a sample of said material into said stream of said carrier fluid flowing to said chromatographic separation column means;
   a dielectric constant detector means;
   a refractive index detector means;
   means for passing the stream of said carrier fluid containing separated components of the sample of said material from said chromatographic separation column means to said dielectric constant detector means as a sample stream;
   means for passing a stream of said carrier fluid to said dielectric constant detector means as a reference stream, said dielectric constant detector means providing a first signal representative of the response $E_{DC}$ of said dielectric constant detector means when the portion of said stream of said carrier fluid containing said substantially non-polar component and the reference stream of said carrier fluid are provided to said dielectric constant detector means;
   means for passing the stream of said carrier fluid containing separated components of said sample of said material from said chromatographic separation column means to said refractive index detector means as a sample stream;
   means for passing a stream of said carrier fluid to said refractive index detector means as a reference stream, said refractive index detector means providing a second signal representative of the response $E_{RI}$ of said refractive index detector means when the portion of said stream of said carrier fluid containing said substantially non-polar component and the reference stream of said carrier fluid are provided to said refractive index detector means; and
   means for establishing the concentration of said substantially non-polar component in response to said first signal and said second signal.

2. Apparatus in accordance with claim 1 wherein said means for establishing the concentration of said substantially non-polar component in response to said first and second signals comprises:

means for establishing a third signal representative of the constant $K_1$ where $$K_1 = \frac{R_E K_{DC}}{P_E K_{RI}}$$

and $R_E$ = molar refraction of said carrier fluid;
$P_E$ = molar polarization of said carrier fluid;
$K_{DC}$ = a constant dependent upon the sensitivity of said dielectric constant detector; and
$K_{RI}$ = a constant dependent upon the sensitivity of said refractive index detector;

means for establishing a fourth signal representative of the constant $K_2$ where $K_2 = K_{DC}(R_E - P_E)/P_E$;
means for multiplying said second signal by said third signal to establish a fifth signal representative of $K_1 E_{RI}$;
means for subtracting said fifth signal from said first signal to establish a sixth signal representative of $E_{DC} - K_1 E_{RI}$; and
means for dividing said sixth signal by said fourth signal to establish the concentration of said substantially non-polar component.

3. Apparatus for obtaining an analysis of the ratio of the molar polarization of a substantially non-polar component in a material to the molar volume of said substantially non-polar component in said material, where the ratio of the molar polarization of said substantially non-polar component in said material to the molar volume of said substantially non-polar component in said material is substantially equal to the ratio of the molar refraction of said substantially non-polar component in said material to the molar volume of said substantially non-polar component in said material, comprising:

a chromatographic separation column means;
means for passing a stream of a carrier fluid, which is substantially polar, to said chromatographic separation column means;
means for injecting a sample of said material into said stream of said carrier fluid flowing to said chromatographic separation column means;
a dielectric constant detector means;
a refractive index detector means;
means for passing the stream of said carrier fluid containing separated components of the sample of said material from said chromatographic separation column means to said dielectric constant detector means as a sample stream;
means for passing a second stream of said carrier fluid to said dielectric constant detector means as a reference stream, said dielectric constant detector means providing a first signal representative of the response $E_{DC}$ of said dielectric constant detector means when the portion of the stream of said carrier fluid containing said substantially non-polar component and the reference stream of said carrier fluid are provided to said dielectric constant detector means;
means for passing the stream of said carrier fluid containing separated components of said sample of said material from said chromatographic separation column means to said refractive index detector means as a sample stream;
means for passing a stream of said carrier fluid to said refractive index detector means as a reference stream, said refractive index detector means providing a second signal representative of the response $E_{RI}$ of said refractive index detector means when the portion of the stream of said carrier fluid containing said substantially non-polar component and the reference stream of said carrier fluid are provided to said refractive index detector means; and
means for establishing the ratio of the molar polarization of said substantially non-polar component in said material to the molar volume of said substantially non-polar component in said material in response to said first signal and said second signal.

4. Apparatus in accordance with claim 3 wherein said means for establishing the ratio of the molar polarization of said substantially non-polar component in said material to the molar volume of said substantially non-polar component in said material in response to said first signal and said second signal comprises:

means for establishing a third signal representative of the constant $K_3$ where $$K_3 = K_{DC}/K_{RI}$$

and $K_{DC}$ = a constant dependent upon the sensitivity of said dielectric constant detector, and
$K_{RI}$ = a constant dependent upon the sensitivity of said refractive index detector;

means for establishing a fourth signal representative of a constant $K_4$ where $$K_4 = \left(\frac{K_{DC}}{K_{RI}}\right)\left(\frac{R_E/V_E}{P_E/V_E}\right)$$

and $R_E$ = molar refraction of said carrier fluid,
$P_E$ = molar polarization of said carrier fluid, and
$V_E$ = volume of said carrier fluid;

means for establishing a fifth signal representative of $R_E/V_E$;
means for multiplying said third signal by said second signal to establish a sixth signal representative of $K_3 E_{RI}$;
means for subtracting said sixth signal from said first signal to establish a seventh signal representative of $E_{DC} - K_3 E_{RI}$;
means for multiplying said seventh signal by said fifth signal to establish an eighth signal representative of $(R_E/V_E)(E_{DC} - K_3 E_{RI})$;
means for multiplying said fourth signal by said second signal to establish a ninth signal representative of $K_4 E_{RI}$;
means for subtracting said ninth signal from said first signal to establish a tenth signal representative of $E_{DC} - K_4 E_{RI}$; and
means for dividing said eighth signal by said tenth signal to establish the ratio of the molar polarization of said substantially non-polar component in said material to the molar volume of said substantially non-polar component.

5. A method for obtaining an analysis of the concentration of a substantially non-polar component of a material comprising the steps of:

utilizing a carrier fluid, which is substantially polar, to perform a chromatographic analysis on said substantially non-polar component from a sample of said material to obtain a first signal representative of the response $E_{DC}$ of a dielectric constant detector and to obtain a second signal representative of the response $E_{RI}$ of a refractive index detector; and establishing the concentration of said substantially non-polar component of said material in response to said first signal and said second signal.

6. A method in accordance with claim 5 wherein said step of establishing the concentration of said substantially non-polar component of said material in response to said first and second signals comprises:

establishing a third signal representative of the constant $K_1$
where $$K_1 = \frac{R_E K_{DC}}{P_E K_{RI}}$$

and $R_E$ = molar refraction of said carrier fluid;
$P_E$ = molar polarization of said carrier fluid;
$K_{DC}$ = a constant dependent upon the sensitivity of said dielectric constant detector; and
$K_{RI}$ = a constant dependent upon the sensitivity of said refractive index detector;

establishing a fourth signal representative of the constant $K_2$
where
$K_2 = K_{DC}(R_E - P_E)/P_E$;
$K_2 = K_{DC}(R_E - P_E)/P_E$;

multiplying said second signal by said third signal to establish a fifth signal representative of $K_1 E_{RI}$;

subtracting said fifth signal from said first signal to establish a sixth signal representative of $E_{DC} - K_1 E_{RI}$; and dividing said sixth signal by said fourth signal to establish the concentration of said substantially non-polar component of said material.

7. A method for obtaining an analysis of the ratio of the molar polarization of a substantially non-polar component in a material to the molar volume of said substantially non-polar component in said material, where the ratio of the molar polarization of said substantially non-polar component in said material to the molar volume of said substantially non-polar component in said material is substantially equal to the ratio of the molar refraction of said substantially non-polar component in said material to the molar volume of said substantially non-polar component in said material, comprising the steps of:

utilizing a carrier fluid, which is substantially polar, to perform a chromatographic analysis on said substantially non-polar component from a sample of said material to obtain a first signal representative of the response $E_{DC}$ of a dielectric constant detector and to obtain a second signal representative of the response $E_{RI}$ of a refractive index detector; and establishing the ratio of the molar polarization of said substantially non-polar component in said material to the molar volume of said substantially non-polar component in said material in response to said first signal and said second signal.

8. A method in accordance with claim 7 wherein said step of establishing the ratio of the molar polarization of said substantially non-polar component in said material to the molar volume of said substantially non-polar component in said material in response to said first signal and said second signal comprises:

establishing a third signal representative of the constant $K_3$
where $$K_3 = K_{DC}/K_{RI}$$

and $K_{DC}$ = a constant dependent upon the sensitivity of said dielectric constant detector, and
$K_{RI}$ = a constant dependent upon the sensitivity of said refractive index detector;

establishing a fourth signal representative of a constant $K_4$
where $$K_4 = \left(\frac{K_{DC}}{K_{RI}}\right)\left(\frac{R_E/V_E}{P_E/V_E}\right)$$

and $R_E$ = molar refraction of said carrier fluid,
$P_E$ = molar polarization of said carrier fluid, and
$V_E$ = molar volume of said carrier fluid;

establishing a fifth signal representative of $R_E/V_E$;

multiplying said third signal by said second signal to establish a sixth signal representative of $K_3 E_{RI}$;

subtracting said sixth signal from said first signal to establish a seventh signal representative of $E_{DC} - K_3 E_{RI}$;

multiplying said seventh signal by said fifth signal to establish an eighth signal representative of $(R_E/V_E)(E_{DC} - K_3 E_{RI})$;

multiplying said fourth signal by said second signal to establish a ninth signal representative of $K_4 E_{RI}$;

subtracting said ninth signal from said first signal to establish a tenth signal representative of $E_{DC} - K_4 E_{RI}$; and dividing said eighth signal by said tenth signal to establish the ratio of the molar polarization of said substantialy non-polar component in said material to the molar volume of said substantially non-polar component in said material.

* * * * *